US009332920B2

(12) United States Patent
Thakur et al.

(10) Patent No.: US 9,332,920 B2
(45) Date of Patent: May 10, 2016

(54) ROTOR IDENTIFICATION USING SEQUENTIAL PATTERN MATCHING

(71) Applicant: Boston Scientific Scimed, Inc., Maple Grove, MN (US)

(72) Inventors: Pramodsingh H. Thakur, Woodbury, MN (US); Barun Maskara, Blaine, MN (US); Shantha Arcot-Krishnamurthy, Renton, WA (US); Sunipa Saha, Shoreview, MN (US); Shibaji Shome, Shoreview, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 168 days.

(21) Appl. No.: 14/134,831

(22) Filed: Dec. 19, 2013

(65) Prior Publication Data

US 2014/0180051 A1    Jun. 26, 2014

Related U.S. Application Data

(60) Provisional application No. 61/739,938, filed on Dec. 20, 2012.

(51) Int. Cl.
*A61B 5/04* (2006.01)
*A61B 5/042* (2006.01)
(Continued)

(52) U.S. Cl.
CPC ............... *A61B 5/042* (2013.01); *A61B 5/0422* (2013.01); *A61B 5/0464* (2013.01);
(Continued)

(58) Field of Classification Search
CPC .... A61B 5/042; A61B 5/0452; A61B 5/7246; A61B 5/7235; A61B 2017/00053; G06K 9/00536; G06K 9/00496; G06K 2209/05
See application file for complete search history.

(56) References Cited

U.S. PATENT DOCUMENTS

| 4,754,753 A | 7/1988 | King |
| 4,799,493 A | 1/1989 | DuFault |

(Continued)

FOREIGN PATENT DOCUMENTS

| WO | WO0045700 A1 | 8/2000 |
| WO | 2006066324 A1 | 6/2006 |

(Continued)

OTHER PUBLICATIONS

Berkowitsch, Alexander et al., "Electrophysiological Heterogeneity of Atrial Fibrillation and Local Effect of Propafenone in the Human Right Atrium: Analysis Based on Symbolic dynamics", Journal of Interventional Cardiac Electrophysiology, Jun. 1, 2000, pp. 383-394.

(Continued)

*Primary Examiner* — Robert N Wieland
(74) *Attorney, Agent, or Firm* — Faegre Baker Daniels LLP (57) ABSTRACT

An anatomical mapping system includes a plurality of mapping electrodes each having an electrode location and configured to detect activation signals of intrinsic physiological activity within an anatomical structure. A mapping processor is associated with the plurality of mapping electrodes and is configured to record the detected activation signals and associate one of the plurality of mapping electrodes with each recorded activation signal. The mapping processor is further configured to analyze the recorded activation signals to identify at least one recurring pattern based on a relationship between a timing of the detected activation signals and the electrode locations of the mapping electrode associated with each detected activation signal.

20 Claims, 6 Drawing Sheets

(51) Int. Cl.

| | |
|---|---|
| *A61B 5/00* | (2006.01) |
| *A61B 5/0464* | (2006.01) |
| *G06K 9/00* | (2006.01) |
| *A61B 18/14* | (2006.01) |
| *A61B 18/00* | (2006.01) |

(52) U.S. Cl.
CPC .......... *A61B 5/6858* (2013.01); *A61B 5/7246* (2013.01); *G06K 9/00536* (2013.01); *A61B 18/1492* (2013.01); *A61B 2018/00357* (2013.01); *A61B 2018/00577* (2013.01); *G06K 2209/057* (2013.01)

(56) References Cited

U.S. PATENT DOCUMENTS

| | | | |
|---|---|---|---|
| 5,038,791 | A | 8/1991 | Collins et al. |
| 5,158,092 | A | 10/1992 | Glace |
| 5,254,088 | A | 10/1993 | Lundquist et al. |
| 5,292,348 | A | 3/1994 | Saumarez et al. |
| 5,433,198 | A | 7/1995 | Desai |
| 5,485,849 | A | 1/1996 | Panescu et al. |
| 5,582,609 | A | 12/1996 | Swanson et al. |
| 5,647,870 | A | 7/1997 | Kordis et al. |
| 5,657,755 | A | 8/1997 | Desai |
| 5,810,740 | A | 9/1998 | Paisner |
| 6,070,094 | A | 5/2000 | Swanson et al. |
| 6,233,491 | B1 | 5/2001 | Kordis et al. |
| 6,574,492 | B1 | 6/2003 | Ben-Haim et al. |
| 6,600,948 | B2 | 7/2003 | Ben-Haim et al. |
| 6,735,465 | B2 | 5/2004 | Panescu |
| 6,950,689 | B1 | 9/2005 | Willis et al. |
| 6,978,168 | B2 | 12/2005 | Beatty et al. |
| 7,841,986 | B2 | 11/2010 | He et al. |
| 2005/0007091 | A1 | 1/2005 | Makeig et al. |
| 2005/0261599 | A1 | 11/2005 | Shvilkin et al. |
| 2006/0074336 | A1 | 4/2006 | Grieve et al. |
| 2006/0116594 | A1 | 6/2006 | Zhang et al. |
| 2007/0299351 | A1 | 12/2007 | Harlev et al. |
| 2008/0222109 | A1* | 9/2008 | Sakurai .............. 707/3 |
| 2011/0251505 | A1 | 10/2011 | Narayan et al. |
| 2012/0184858 | A1 | 7/2012 | Harlev et al. |
| 2012/0296569 | A1 | 11/2012 | Shahaf et al. |
| 2014/0336518 | A1 | 11/2014 | Shuros et al. |
| 2014/0343388 | A1 | 11/2014 | Thakur et al. |
| 2014/0371616 | A1* | 12/2014 | Narayan et al. .......... 600/518 |

FOREIGN PATENT DOCUMENTS

| | | |
|---|---|---|
| WO | 2012092016 A1 | 7/2012 |
| WO | 2013123549 A1 | 8/2013 |
| WO | 2014100464 A1 | 6/2014 |

OTHER PUBLICATIONS

Ciaccio, Edward J. et al., "Identification of recurring patterns in fractionated atrial electrograms using new transform coefficients", Biomedical engineering Online, vol. 11, No. 1, Jan. 1, 2012, 19 pages.

Fitzgerald, Tamara N. et all, "Identification of Cardiac Rhythm Features by Mathematical Analysis of Vector Fields", IEEE Transactions on Biomedical Engineering, vol. 52, No. 1, Jan. 2005, pp. 19-29.

International Search Report and Written Opinion issued in PCT/US2013/076667, mailed Mar. 20, 2014, 14 pages.

Marbroukeh, Nizar R. et al., "A Taxonomy of Sequential Pattern Mining Algorithms", ACM Computing Surveys, vol. 43, No. 1, Nov. 1, 2010, pp. 1-41.

Masse, Stephane et al., "Wave similarity of human ventricular fibrillation from bipolar electrograms", Europace, vol. 9, No. 1, Jan. 1, 2007, 10 pages.

Barbaro. V., et, al. Measure of Synchronisation of Right Atrial Depolarisation Wayefronts During Atrial Fibrillation. Med. Biol. Eng. Comput., 40(1): 56-62, 2002.

Brodda, K., et. al. A New Method for Detection of P Waves in Electrocardiograms. Signal Processing, 1(1): 15-25, 1979.

Habel, N., et. al. The Temporal Variability of Dominant Frequency and Complex Fractionated Atrial Electrograms Constrains the Validity of Sequential Mapping in Human Atrial Fibrillation. Heart Rhythm, 7:586-593, 2010.

Holm, Magnus et al. A New Method for Analysis of Atrial Activation During Chronic Atrial Fibrillation in Man, IEEE Transactions on Biomedical Engineering, 43(2): 198-210, Feb. 1996.

Houben, Richard P.M. et al., "Processing Intracardiac Electrograms in Atrial Fibrillation", Diagosis of Eiectropathologicai Substrate of AF, IEEE Engineering in Medicine and Biology Magazine, Nov./Dec. 2006.

International Preliminary Report on Patentability issued in PCT/US2013/076667, mailed Jul. 2, 2015, 9 pages.

International Search Report and Written Opinion issued in PCT/US2014/038357, mailed Sep. 1, 2014, 11 pages.

International Search Report and Written Opinion issued in PCT/US2014/062876, mailed Feb. 11, 2015, 12 pages.

International Search Report and Written Opinion issued in PCT/US2015/036746, mailed Sep. 1, 2015, 12 pages.

International Search Report and Written Opinion] issued in PCT/US2014/053147, mailed Nov. 7, 2014, 12 pages.

Jadidi, A., et. al, Functional Nature of Electrogram Fractionation Demonstrated by Left Atrial High-Density Mapping. Circ. Arrhythm Electrophysiol., 5:32-42, 2012.

Rogers, Jack m et al., Recurrent Wavefront Morphologies: A Method for Quantifying the Complexity of Epicardial Activation Patterns, Annals of Biomedical Engineering, vol. 25, No. 5, 1997, pp. 761-768.

Sanders et al., "Spectral Analysis Identifies Sites of High-Frequency Activity Maintaining Atrial Fibriiiation in Humans", Circulation, 112:789-797, 2005.

* cited by examiner

ROTOR IDENTIFICATION USING SEQUENTIAL PATTERN MATCHING

CROSS-REFERENCE TO RELATED APPLICATIONS

This application claims the benefit under 35 U.S.C. §119 (e) to U.S. Provisional Application 61/739,938, entitled "ROTOR IDENTIFICATION USING SEQUENTIAL PATTERN MATCHING", filed on Dec. 20, 2012, which is herein incorporated by reference in its entirety.

TECHNICAL FIELD

The present disclosure relates to cardiac mapping systems. More specifically, the present disclosure relates to a cardiac mapping system configured to identify aberrant conductive pathways and corresponding focal sources using pattern recognition.

BACKGROUND

Diagnosing and treating heart rhythm disorders often involve the introduction of a catheter having a plurality of sensors/probes into a cardiac chamber through the surrounding vasculature. The sensors detect electric activity of the heart at sensor locations in the heart. The electric activity is generally processing into electrogram signals that represent signal propagation through cardiac tissue at the sensor locations Physicians often examine the propagation pathways to locate aberrant conduction pathways and to identify arrhythmia focal points. Cardiac ablation is one interventional treatment used to treat many heart rhythm disorders such as atrial fibrillation, atrial flutter, AV re-entrant tachycardia, ventricular tachycardia, and the like. Typically, a radiofrequency (RF) ablation catheter is used to destroy the pathological conduction tissue which forms the aberrant conduction pathways. The ablation procedure disconnects the aberrant conduction pathways from the surround conductive pathways thus returning the patient to a healthy cardiac rhythm.

SUMMARY

Disclosed herein are various embodiments of a method for identifying patterns in intrinsic cardiac activation signals sensed by a cardiac catheter, as well as anatomical mapping systems employing such methods.

In Example 1, an anatomical mapping system includes a plurality of mapping electrodes each having an electrode location and configured to detect activation signals of intrinsic physiological activity within an anatomical structure. A mapping processor is associated with the plurality of mapping electrodes and is configured to record the detected activation signals and associate one of the plurality of mapping electrodes with each recorded activation signal. The mapping processor is further configured to analyze the recorded activation signals to identify at least one recurring pattern based on a relationship between a timing of the detected activation signals and the electrode locations of the mapping electrode associated with each detected activation signal.

In Example 2, the anatomical mapping system according to Example 1, wherein the mapping processor is further configured to determine a location of the at least one recurring pattern with respect to the anatomical structure.

In Example 3, the anatomical mapping system according to either Example 1 or Example 2, wherein the mapping processor is further configured to correlate the at least one recurring pattern to at least one pathology template to determine whether the at least one recurring pattern is indicative of a pathology.

In Example 4, the anatomical mapping system according to Example 3, wherein the mapping processor is configured to correlate the at least one recurring pattern to the at least one pathology template based on activation signals detected by a subset of the plurality of mapping electrodes.

In Example 5, the anatomical mapping system according to any of Examples 1-4, wherein the mapping processor is configured to run a sequential mining algorithm on the detected activation signals to identify at least one recurring pattern.

In Example 6, the anatomical mapping system according to any of Examples 1-5, wherein the mapping processor is configured to run a location association mining algorithm on the detected activation signals to identify at least one recurring pattern.

In Example 7, a catheter system includes a plurality of mapping electrodes each having an electrode location and configured to detect activation signals of intrinsic cardiac activity. A mapping processor is associated with the plurality of mapping electrodes and is configured to record the detected activation signals and associate one of the plurality of mapping electrodes with each recorded activation signal. The mapping processor further configured to analyze the recorded activation signals to identify at least one recurring pattern based on a relationship between a timing of the detected activation signals and the electrode locations of the mapping electrode associated with each detected activation signal.

In Example 8, the catheter system according to Example 7, wherein the mapping processor is further configured to determine a location of the at least one frequently occurring pattern based on the location of the mapping electrodes and the corresponding detected activation signals.

In Example 9, the catheter system according to either Example 7 or Example 8, wherein the mapping processor is further configured to correlate the at least one recurring pattern to at least one rotor template to determine whether the at least one recurring pattern is indicative of a dominant rotor.

In Example 10, the catheter system according to any of Examples 7-9, wherein the rotor template is characteristic of at least one of a dominant rotor, rotor core, and rotor pathway having a cyclical and/or curvilinear pathway.

In Example 11, the catheter system according to any of Examples 7-10, wherein the mapping processor is configured to correlate the at least one recurring pattern to the at least one rotor template based on activation signals detected by a subset of the plurality of mapping electrodes.

In Example 12, the catheter system according to any of Examples 7-11, wherein the mapping processor is configured to run a sequential mining algorithm on the detected activation signals to identify at least one recurring pattern.

In Example 13, the catheter system according to any of Examples 7-12, wherein the mapping processor is configured to run a location association mining algorithm on the detected activation signals to identify at least one recurring pattern.

In Example 14, the catheter system according to any of Examples 7-13, wherein the mapping processor is configured to run a location association mining algorithm and a sequential mining algorithm on the detected activation signals to identify at least one recurring pattern.

In Example 15, a method for anatomical mapping includes positioning a plurality of mapping electrodes proximate to an anatomical structure, each of the plurality of mapping electrodes having an electrode location, detecting activation signals of intrinsic physiological activity within the anatomical structure, recording the detected activation signals and associating one of the plurality of mapping electrodes with each recorded activation signal, and analyzing the recorded activation signals to identify at least one recurring pattern based on a relationship between a timing of the detected activation signals and the electrode locations of the mapping electrode associated with each detected activation signal.

In Example 16, the method according to Example 15, and further including determining a location of the at least one recurring pattern with respect to the anatomical structure.

In Example 17, the method according to either Example 15 or Example 16, and further including correlating the at least one recurring pattern to at least one pathology template to determine whether the at least one recurring pattern is indicative of a pathology In Example 18, the method according to any of Examples 15-17, wherein the at least one recurring pattern is correlated to the at least one pathology template based on activation signals detected by a subset of the plurality of mapping electrodes.

In Example 19, the method according to any of Examples 15-18, wherein a sequential mining algorithm is performed on the detected activation signals to identify the at least one recurring pattern.

In Example 20, the method according to any of Examples 15-19, wherein a location association mining algorithm is performed on the detected activation signals to identify at least one recurring pattern.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
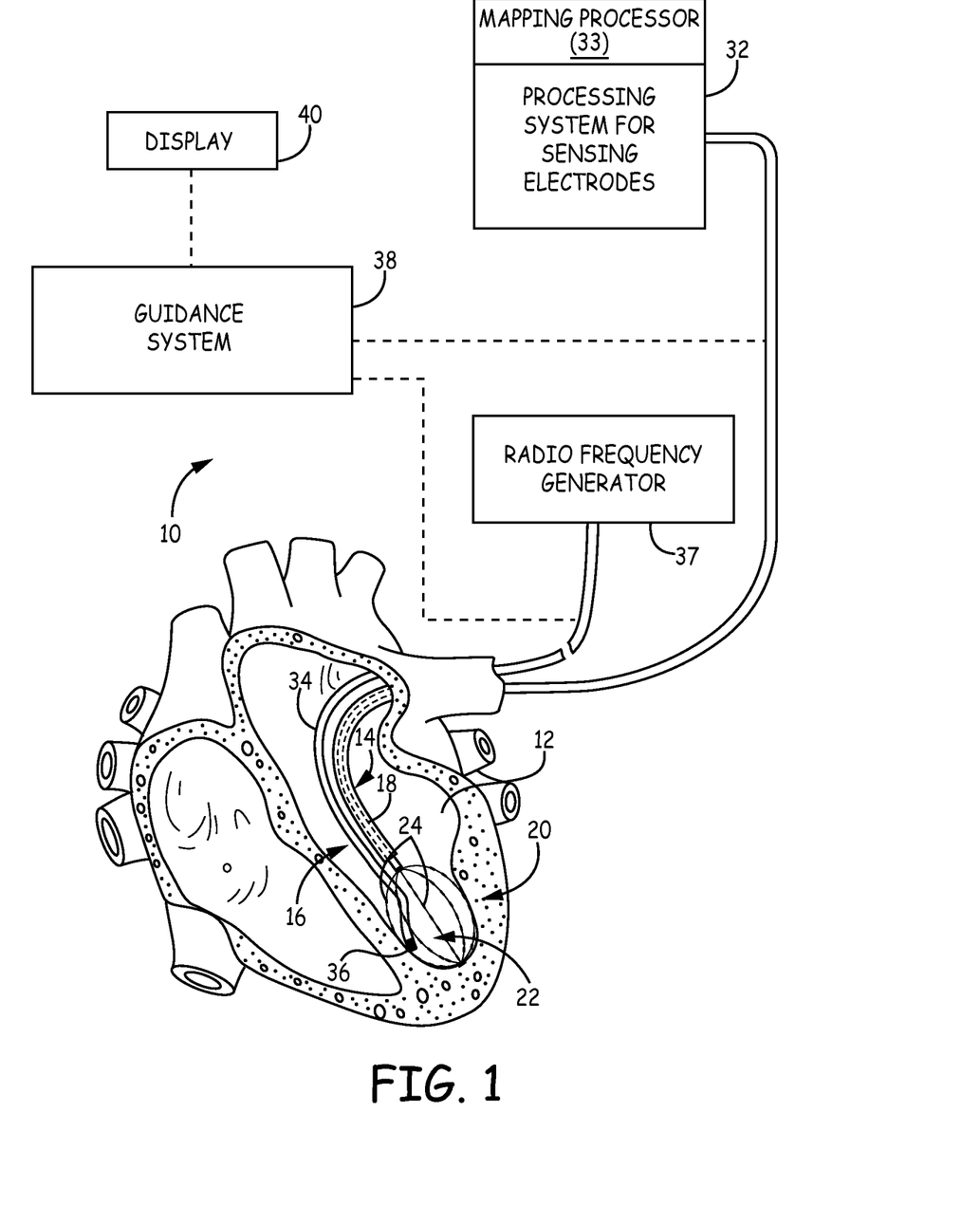
FIG. 1 is a schematic view of an embodiment of a system for accessing a targeted tissue region in the body for diagnostic and therapeutic purposes.

FIG. 1 is a schematic view of a system 10 for accessing a targeted tissue region in the body for diagnostic or therapeutic purposes. FIG. 1 generally shows the system 10 deployed in the left ventricle of the heart. Alternatively, system 10 can be deployed in other regions of the heart, such as the left atrium, right atrium, or right ventricle. While the illustrated embodiment shows the system 10 being used for ablating myocardial tissue, the system 10 (and the methods described herein) may alternatively be configured for use in other tissue ablation applications, such as procedures for ablating tissue in the prostrate, brain, gall bladder, uterus, and other regions of the body, including in systems that are not necessarily catheter-based.

The system 10 includes a mapping probe 14 and an ablation probe 16. In FIG. 1, each is separately introduced into the selected heart region 12 through a vein or artery (e.g., the femoral vein or artery) through suitable percutaneous access. Alternatively, the mapping probe 14 and ablation probe 16 can be assembled in an integrated structure for simultaneous introduction and deployment in the heart region 12.

The mapping probe 14 has a flexible catheter body 18. The distal end of the catheter body 18 carries a three-dimensional multiple electrode structure 20. In the illustrated embodiment, the structure 20 takes the form of a basket defining an open interior space 22 (see FIG. 2), although other multiple electrode structures could be used wherein the geometry of the electrode structure and electrode locations are known. The multiple electrode structure 20 carries a plurality of electrodes 24 wherein each is configured to sense intrinsic physiological activity in the anatomical region on which the ablation procedure is to be performed. In some embodiments, the electrodes are configured to detect activation signals of the intrinsic physiological activity within the anatomical structure, e.g., the activation times of cardiac activity.

The electrodes 24 are electrically coupled to a processing system 32. A signal wire (not shown) is electrically coupled to each electrode 24 on the basket structure 20. The wires extend through the body 18 of the probe 14 and electrically couple each electrode 24 to an input of a mapping processor 33 of the processing system 32, as will be described later in greater detail. The electrodes 24 sense intrinsic electrical activity in the anatomical region, e.g., myocardial tissue. The sensed activity is processed by the mapping processor 33 to assist the physician in identifying the site or sites within the heart appropriate for ablation. A mapping processor 33 collects and mines the physiological activity data (e.g., activation times of cardiac activity) to identify at least one recurring pattern, i.e. a sequential, locational, and/or temporal recurring pattern. The identified recurring patterns are correlated to predetermined templates indicative of a pathology to determine a location suitable for ablation for treatment of the pathology.

In some embodiments, the processing system 32 may be configured to measure the intrinsic electrical activity in the myocardial tissue adjacent to the electrodes 24. For example, in some embodiments, the processing system 32 is configured to detect intrinsic electrical activity associated with a dominant rotor in the anatomical feature being mapped. Studies have shown that dominant rotors have a role in the initiation and maintenance of atrial fibrillation, and ablation of the rotor path and/or rotor core may be effective in terminating the atrial fibrillation. In either situation, the mapping processor 33 processes the sensed activation time information to derive the location of a myocardial site appropriate for ablation using the ablation probe 16. The predetermined pathology templates are configured to be representative of a dominant rotor, rotor core, or rotor pathway. For example, the pathology templates may be configured to identify a clockwise or counter-clockwise cyclical pattern typically associated with a dominant rotor and its corresponding rotor core. The processing system 32 labels a location on or in the anatomical structure indicative of the pathology as a candidate for ablation therapy applied by the ablation probe 16.

The ablation probe 16 includes a flexible catheter body 34 that carries one or more ablation electrodes 36. The one or more ablation electrodes 36 are electrically connected to a radio frequency generator (RF) 37 that is configured to deliver ablation energy to the one or more ablation electrodes 36. The ablation probe 16 is movable with respect to the anatomical feature to be treated, as well as the structure 20. The ablation probe 16 is positionable between or adjacent to electrodes 24 of the structure 20 as the one or more ablation electrodes 36 are positioned with respect to the tissue to be treated.

A guidance system 38 is electrically coupled to the processing system 32 and the ablation catheter 16. The guidance system 38 provides a position-identifying output that aids the physician in guiding the ablation electrode(s) 36 into contact with tissue at the site identified as a candidate for ablation therapy by the processing system 32. The guidance system 38 outputs to a display 40 the current location of the ablation catheter relative to the identified ablation sites.

In the illustrated embodiment, the guidance system 38 includes an output display device 40 (e.g., a CRT, LED display, or a printer). The device 40 presents the position-identifying output in a real-time format most useful to the physician for remotely guiding the ablation electrode 36 within the basket structure 20.

Figure 2:
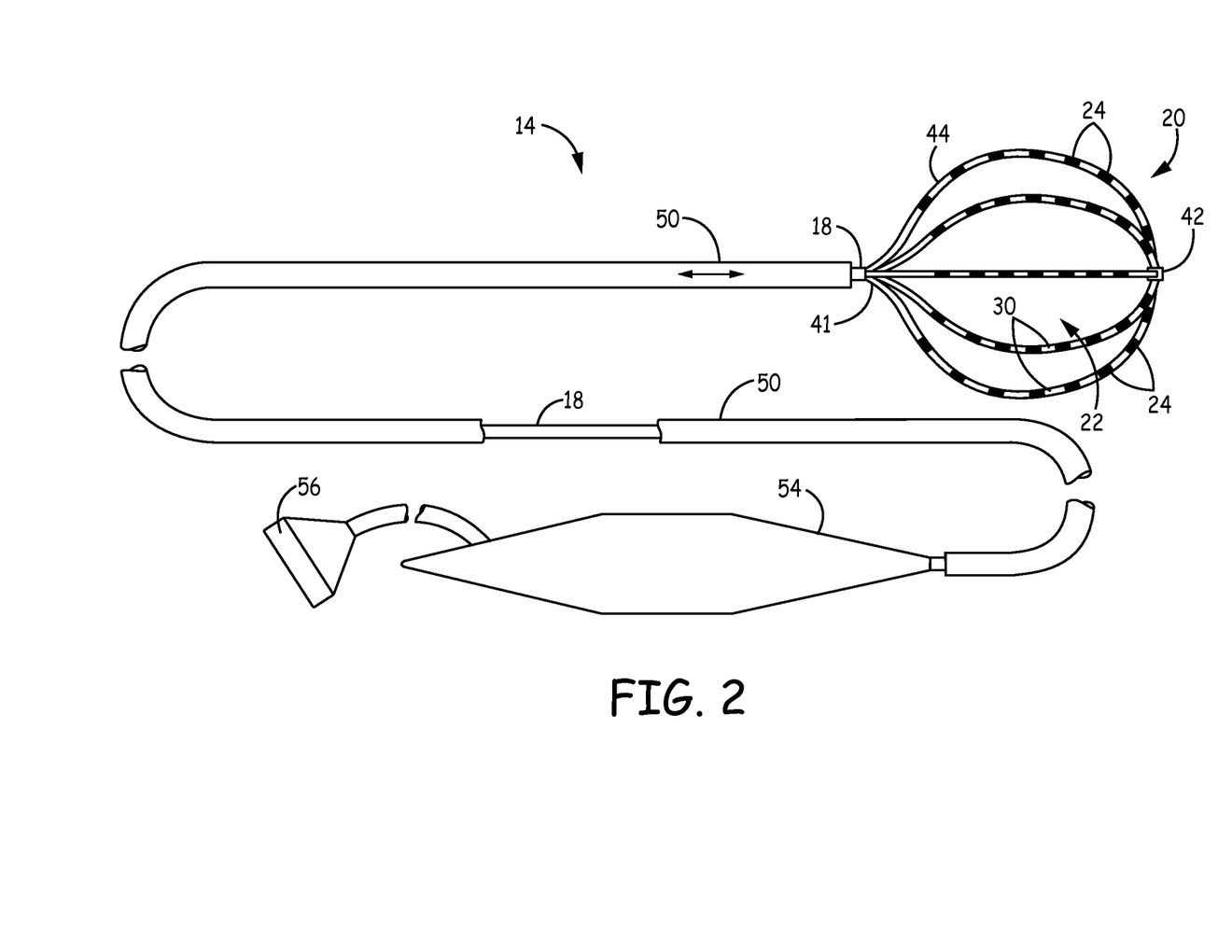
FIG. 2 is a schematic view of an embodiment of a mapping catheter having a basket functional element carrying structure for use in association with the system of FIG. 1.

FIG. 2 illustrates an embodiment of the mapping catheter 14 including electrodes 24 at the distal end suitable for use in the system 10 shown in FIG. 1. The mapping catheter 14 has a flexible catheter body 18, the distal end of which carries the three dimensional structure 20 configured to carry the mapping electrodes or sensors 24. The mapping electrodes 24 sense intrinsic electrical activity in the myocardial tissue, the sensed activity is then processed by the processing system 32 and guidance system 38 to assist the physician in identifying the site or sites having a heart rhythm disorder or other myocardial pathology. This process is commonly referred to as mapping. This information can then be used to determine an appropriate location for applying appropriate therapy, such as ablation, to the identified sites, and to navigate the one or more ablation electrodes 36 to the identified sites.

The illustrated three-dimensional structure 20 comprises a base member 41 and an end cap 42 between which flexible splines 44 generally extend in a circumferentially spaced relationship. As discussed above, the three dimensional structure 20 takes the form of a basket defining an open interior space 22. In some embodiments, the splines 44 are made of a resilient inert material, such as Nitinol metal or silicone rubber, and are connected between the base member 41 and the end cap 42 in a resilient, pretensed condition, to bend and conform to the tissue surface they contact. In the illustrated embodiment, eight splines 44 form the three dimensional structure 20. Additional or fewer splines 44 could be used in other embodiments. As illustrated, each spline 44 carries eight mapping electrodes 24. Additional or fewer mapping electrodes 24 could be disposed on each spline 44 in other embodiments of the three dimensional structure 20. In the illustrated embodiment, the three dimensional structure 20 is relatively small (e.g., 40 mm or less in diameter). In alternative embodiments, the three dimensional structure 20 is larger (e.g., 40 mm in diameter or greater).

A slidable sheath 50 is movable along the major axis of the catheter body 30. Moving the sheath 50 forward (i.e., toward the distal end) causes the sheath 50 to move over the three dimensional structure 20, thereby collapsing the structure 20 into a compact, low profile condition suitable for introduction into an interior space, such as, for example, into the heart. In contrast, moving the sheath 50 rearward (i.e., toward the proximal end) exposes the three dimensional structure 20, allowing the structure 20 to elastically expand and assume the pretensed position illustrated in FIG. 2. Further details of embodiments of the three dimensional structure 20 are disclosed in U.S. Pat. No. 5,647,870, entitled "Multiple Electrode Support Structures," which is hereby incorporated by reference in its entirety.

A signal wire (not shown) is electrically coupled to each mapping electrode 26. The wires extend through the body 30 of the mapping catheter 20 into a handle 54, in which they are coupled to an external connector 56, which may be a multiple pin connector. The connector 56 electrically couples the mapping electrodes 24 to the processing system 32 and guidance system 38. Further details on mapping systems and methods for processing signal generated by the mapping catheter are discussed in U.S. Pat. No. 6,070,094, entitled "Systems and Methods for Guiding Movable Electrode Elements within Multiple-Electrode Structure," U.S. Pat. No. 6,233,491, entitled "Cardiac Mapping and Ablation Systems," and U.S. Pat. No. 6,735,465, entitled "Systems and Processes for Refining a Registered Map of a Body Cavity," the disclosures of which are incorporated herein by reference.

It is noted that other multi-electrode structures could be deployed on the distal end. It is further noted that the multiple mapping electrodes 24 may be disposed on more than one structure rather than, for example, the single mapping catheter 14 illustrated in FIG. 2. For example, if mapping within the left atrium with multiple mapping structures, an arrangement comprising a coronary sinus catheter carrying multiple mapping electrodes and a basket catheter carrying multiple mapping electrodes positioned in the left atrium may be used. As another example, if mapping within the right atrium with multiple mapping structures, an arrangement comprising a decapolar catheter carrying multiple mapping electrodes for positioning in the coronary sinus, and a loop catheter carrying multiple mapping electrodes for positioning around the tricuspid annulus may be used.

Although the mapping electrodes 24 have been described as being carried by dedicated mapping probes, such as the mapping catheter 14, the mapping electrodes may be carried on non-mapping dedicated probes or multifunction probes. For example, an ablation catheter, such as the ablation catheter 16, can be configured to include one or more mapping electrodes 24 disposed on the distal end of the catheter body and coupled to the signal processing system 32 and guidance system 38. As another example, the ablation electrode at the distal end of the ablation catheter may be coupled to the signal processing system 32 and guidance system 38 to also operate as a mapping electrode.

Figure 3:
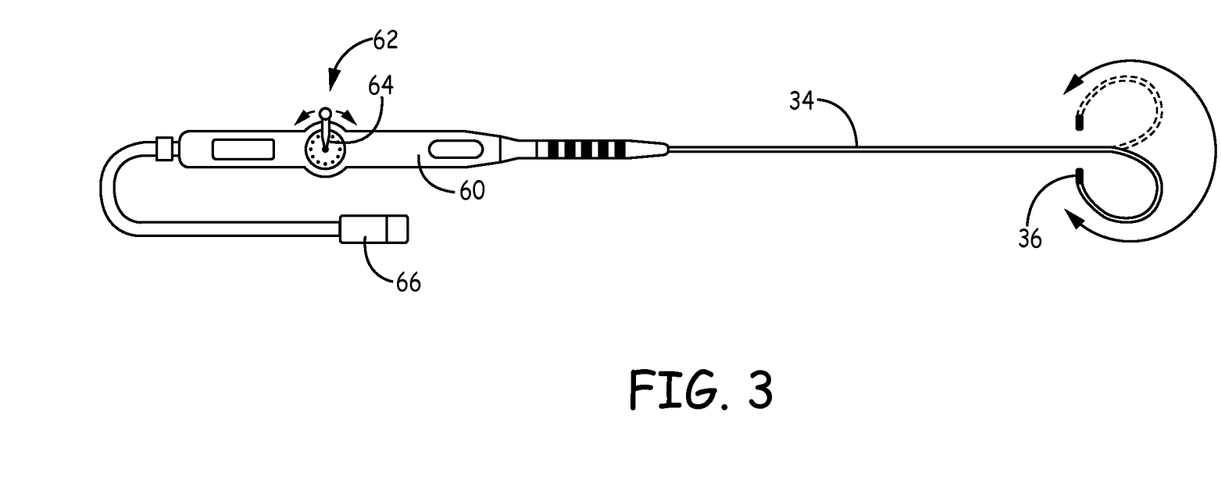
FIG. 3 is a schematic view of an embodiment of an ablation catheter for use in association with the system of FIG. 1.

FIG. 3 is a schematic view of an embodiment of the ablation catheter 16 for use in association with the system of FIG. 1. For the sake of illustration, FIG. 1 shows a single ablation electrode 36 carried at the distal tip of the catheter body 34. Other configurations employing multiple ablation electrodes are possible, as described in U.S. Pat. No. 5,582,609, entitled "Systems and Methods for Forming Large Lesions in Body Tissue Using Curvilinear Electrode Elements," which is hereby incorporated by reference in its entirety.

A handle 60 is attached to the proximal end of the catheter body 34. The handle 60 and catheter body 34 carry a steering mechanism 62 for selectively bending or flexing the catheter body 34 along its length, as the arrows in FIG. 3 show. In the illustrated embodiment, the steering mechanism 62 includes a rotating cam wheel with an external steering lever 64. Movement of the steering lever 64 flexes the distal end of the body 34 to bring the electrode 36 into conforming, intimate contact against the endocardial tissue. One exemplary steering mechanism is shown and described in U.S. Pat. No. 5,254,088, which is hereby incorporated by reference in its entirety.

A wire (not shown) electrically connected to the ablation electrode 36 extends through the catheter body 34 into the handle 60, where it is electrically coupled to an external connector 66. With reference to FIGS. 1 and 3, the connector 66 connects the ablation electrode 36 to the RF generator 37 and to the guidance system 38. During an ablation procedure, the physician positions the ablation electrode 36 in contact with myocardial tissue at the site identified by the guidance system 38 for ablation. Once positioned, the physician directs the RF generator 37 to supply the ablation electrode with a predetermined amount of ablation energy. In response, the ablation electrode 36 emits ablating energy to cauterize the contacted tissue and disrupt the abnormal electrical pathways.

Figure 4:
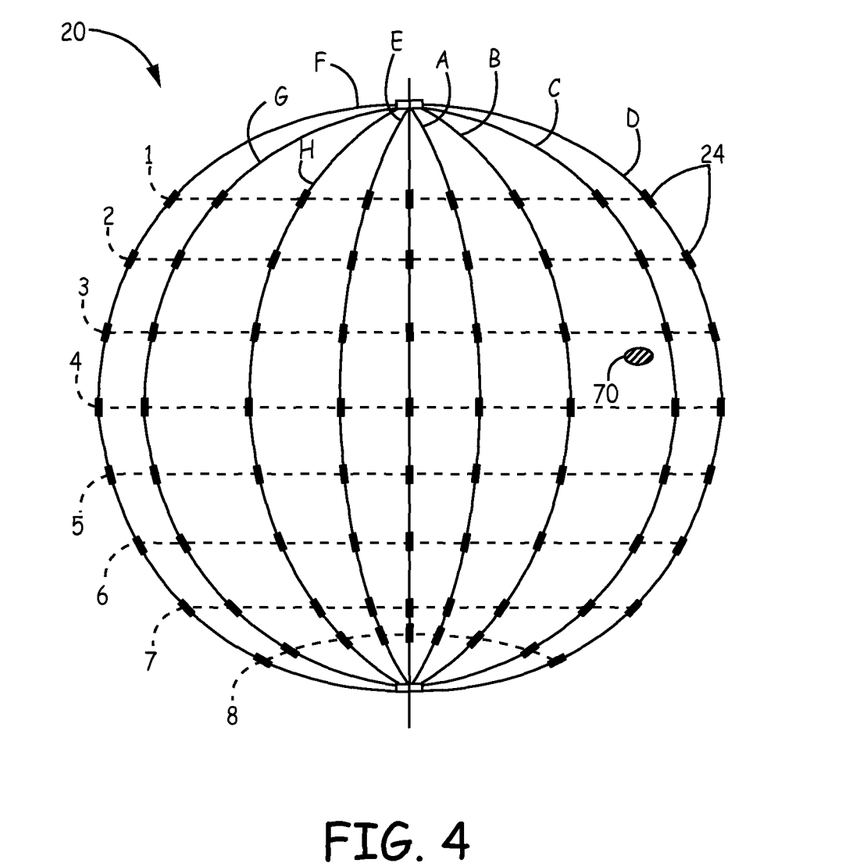
FIG. 4 is a schematic side view of an embodiment of the basket functional element including a plurality of mapping electrodes.

To illustrate the operation of the system 10, FIG. 4 is a schematic side view of an embodiment of the basket structure 20 including a plurality of mapping electrodes 24. In the illustrated embodiment, the basket structure includes 64 mapping electrodes 24. The mapping electrodes 24 are disposed in groups of eight electrodes (labeled 1, 2, 3, 4, 5, 6, 7, and 8) on each of eight splines (labeled A, B, C, D, E, F, G, and H). While an arrangement of sixty-four mapping electrodes 24 is shown disposed on a basket structure 20, the mapping electrodes 24 may alternatively be arranged in different numbers, on different structures, and/or in different positions. In addition multiple basket structures can be deployed in the same or different anatomical structures to simultaneously obtain signals from different anatomical structures.

After the basket structure 20 is positioned adjacent to the anatomical structure to be treated (e.g., left atrium, left ventricle, right atrium, or right ventricle of the heart), the processing system 32 receive activation signals from the electrodes 24 related to intrinsic physiological activity of the anatomical structure, i.e. the electrodes 24 measure electrical activation signals intrinsic to the physiology of the anatomical structure. The mapping processor 32 is configured to detect patterns, e.g. sequential, locational, and/or temporal patterns, among the detected activation signals to identify and/or indicate a pathology such as, for example, a dominant rotor, rotor path, and/or a rotor core.

Figure 5:
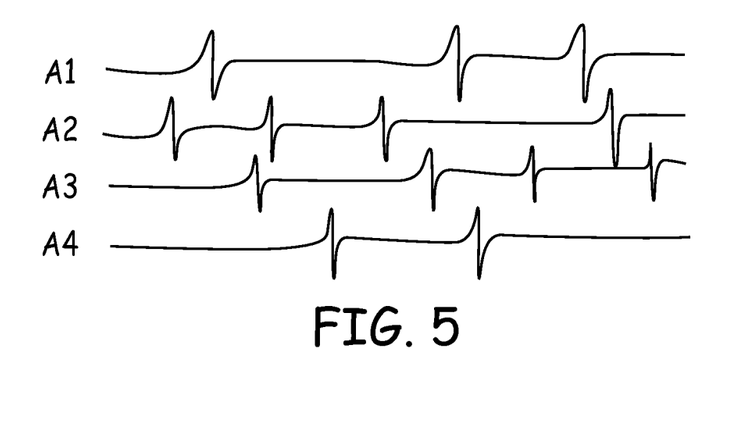
FIG. 5 illustrates waveforms representative of activation times detected by electrodes in the basket functional element.

The mapping processor 33 is configured to algorithmically mine the detected activation signals for sequential pattern searches. In some embodiments, activation signals are detected at each electrode location and recorded as an ordered sequential string. For example, FIG. 5 illustrates a plurality of waveforms representative of activation signals detected by a plurality of electrodes in the basket structure 20. In the illustrated embodiment, signals from four electrodes, A1, A2, A3, and A4, are illustrated. As is shown, the electrodes A1-A4 sense activation signals in the order <A2, A1, A3, A2, A4, A2, A3, A1, A4, A3, A1, A2, A3>. The mapping processor 33 is configured to perform a sequential mining algorithm to identify at least one recurring sequential pattern based on a correlation between the timing of the detected activation signal and the electrode location(s) of the detected activation signal.

Figure 6:
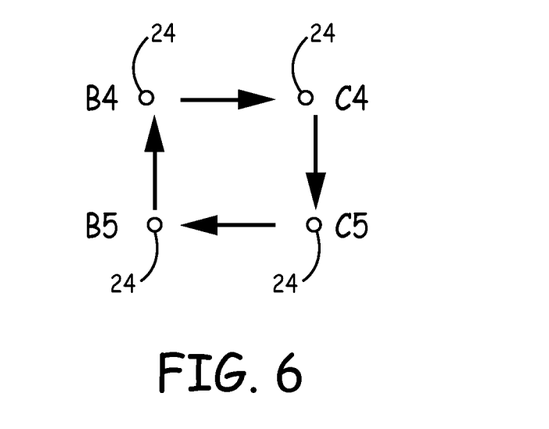
FIG. 6 illustrates a recurring activation pattern based on the location of activation signals with respect to a plurality of electrodes in the basket functional element.

To illustrate an activation sequence that has a pattern, FIG. 6 illustrates four electrodes from the basket structure 20, B4, B5, C4, and C5, that sense an activation signal sequentially in a rotating pattern. In particular, the illustrated electrodes sense the cyclical sequential pattern of <C4, C5, B5, B4> as the electrodes sense temporally spaced activation signals. The activation sequence can also be identified as <C4, C5, B5, B4>, <C5, B5, B4, C4>, <B5, B4, C4, C5>, or <B4, C4, C5, B5>. In some embodiments, when the mapping processor 33 detects multiple instances of any one of the representations of the illustrated sequential pattern, the mapping processor identifies the sequential pattern as a recurring sequential pattern. In another embodiment the frequency of occurrence of a particular sequential pattern can be compared to that expected by chance. For example, 24 ordered sequences are possible between 4 electrodes, so all things being equal any sequential pattern over 4 electrodes has a likelihood of appearing 100/24% of the times. In some embodiments, the identified recurring sequential patterns are correlated to at least one pathology template to determine whether the identified recurring sequential pattern is indicative of a pathology. For example, a cyclical or curvilinear sequential pattern maybe indicative of a rotor core or rotor pathway, respectively, which may indicate the presence of a fibrillation event.

Figure 7:
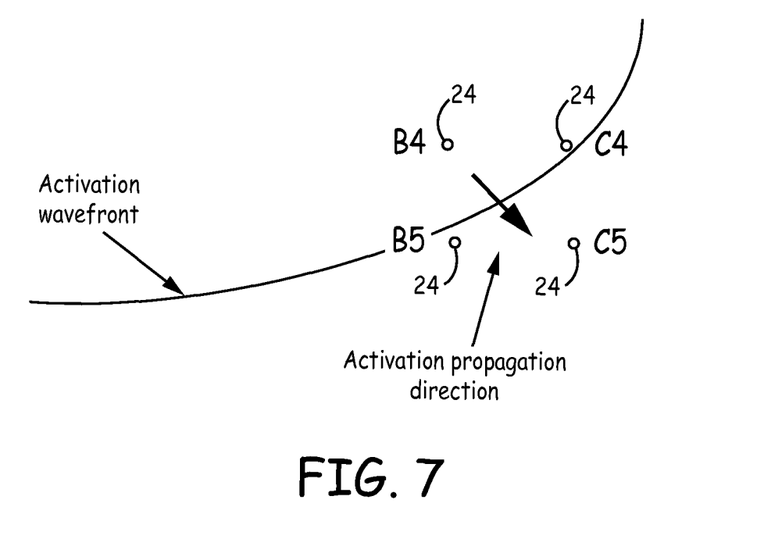
FIG. 7 illustrates a recurring activation pattern based on the movement of activation signals over time with respect to a plurality of electrodes in the basket functional element.

In another example, FIG. 7 illustrates electrodes B4, B5, C4, and C5, and a wavefront of an activation signal moving with respect to the electrodes. In this case, a curvilinear rotor path is illustrated wherein the time interval between activations of neighboring or adjacent mapping electrodes 24 is indicative of their alignment with respect to a rotor path. Electrodes parallel to the rotor path will detect a corresponding activation signal substantially simultaneously, e.g. electrode B5 and C4, whereas electrodes orthogonal to the rotor path will detect the corresponding activation signals after a temporal latency, e.g. electrodes B4 and C5, which can be estimated according to the conduction velocity of the activation signal and the inter-electrode distance.

In some embodiments, the mapping processor 33 performs a location association mining algorithm to identify at least one recurring association pattern based on a correlation between the timing of the detected activation signal and the electrode location(s) of the detected activation signal. The mapping processor 33 identifies recurring association patterns according to substantially simultaneous activation signals, i.e., activation signals detected in close spatial and/or temporal proximity are identified as associated. The frequency of occurrence of the recurring association patterns is compared to an expectation of random occurrences of association patterns with respect to a small subset of mapping electrodes 24. The recurring association patterns are correlated to at least one pathology template to determine whether the identified recurring sequential pattern is indicative of a pathology. For example, a cyclical or curvilinear sequential pattern maybe indicative of a rotor core or rotor pathway, respectively.

In some embodiments, the mapping processor 33 performs a sequential mining algorithm. The sequential mining algorithm may be performed in concert with or in lieu of a location association mining algorithm. The outcomes of the respective algorithms are correlated to determine a confidence index of an identified pathology. Identified pathologies with high confidence indices are deemed suitable for ablation therapy. It should be noted that the sequential and location association mining algorithms can be performed on activation signals acquired by all or a subset of the mapping electrodes 24 in order to reduce the computational cost and/or time.

The processing system 32 determines at least one pathology location 70 based on the mapping electrode 24 locations associated with the identified recurring pattern, sequential and/or association, indicative of a pathology. The pathology location 70 is outputted to the guidance system 38 which outputs the pathology location 70 to the display 40. A physician directs the ablation electrode 36 of the ablation catheter 16 relative to the basket structure 20 until the ablation electrode 36 is positioned adjacent to or against the pathology location 70 to be treated proximate to the basket structure 20. The ablation electrode 36 may pass through the interior space 22 of the basket structure 20 to reach the anatomical structure to be treated. For example, in the embodiment illustrated in FIG. 4, the ablation electrode 36 is disposed against the anatomical structure between the mapping electrodes B3, B4, C3, and C4 to treat the pathology location 70. When the ablation electrode 36 is located in the desired position, ablation energy may be delivered to the ablation electrode 36 to ablate the target tissue of the anatomical structure.

In an exemplary embodiment, the mapping electrodes 24 are configured to sense and provide activation signals related to a rotor in the atrium of the heart, which are provided to the processing system 32. The mapping processor 33 then mines the received activation signals for recurring activation patterns, i.e. sequential patterns and/or location association patterns, according to at least one of a sequential mining algorithm and a location associate mining algorithm. The mapping processor 33 correlates the identified recurring patterns to rotor templates to identify which recurring patterns are indicative of a dominant rotor, rotor core, and/or a rotor pathway. The rotor templates are characteristic of a cyclical or a curvilinear recurring pattern which is typically indicative of a dominant rotor. The processing system 32 determines a rotor location 70 of the identified recurring patterns indicative of a dominant rotor according to mapping electrode 24 locations corresponding to the identified recurring patterns. The processing system 32 provides the rotor locations 70 to the guidance system 38. The guidance system 38 outputs the rotor location 70 relative to the ablation electrode 36 location to a display unit 40 to aid a physician in placing the ablation electrode 36 in the desired location. When in the desired location, ablation energy can be delivered to the ablation electrode 36 to ablate the rotor path or core.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An anatomical mapping system comprising:
    a plurality of mapping electrodes configured to detect activation signals of intrinsic physiological activity within an anatomical structure, each of the plurality of mapping electrodes having an electrode location;
    a mapping processor associated with the plurality of mapping electrodes, the mapping processor configured to record the detected activation signals and associate one of the plurality of mapping electrodes with each recorded activation signal, the mapping processor further configured to analyze the recorded activation signals to identify at least one recurring pattern of the detected activation signals sensed by mapping electrodes at different electrode locations based on a relationship between a timing of the detected activation signals and the electrode locations of the mapping electrode associated with each detected activation signal.

2. The anatomical mapping system according to claim 1, wherein the mapping processor is further configured to determine a location of the at least one recurring pattern with respect to the anatomical structure.

3. The anatomical mapping system according to claim 1, wherein the mapping processor is further configured to correlate the at least one recurring pattern to at least one pathology template to determine whether the at least one recurring pattern is indicative of a pathology.

4. The anatomical mapping system according to claim 3, wherein the mapping processor is configured to correlate the at least one recurring pattern to the at least one pathology template based on activation signals detected by a subset of the plurality of mapping electrodes.

5. The anatomical mapping system according to claim 1, wherein the recurring pattern is a recurring sequential pattern and the mapping processor is configured to run a sequential mining algorithm on the detected activation signals to identify at least one recurring pattern.

6. The anatomical mapping system according to claim 1, wherein the recurring pattern is a recurring association pattern and the mapping processor is configured to run a location association mining algorithm on the detected activation signals to identify at least one recurring pattern.

7. A catheter system comprising:
    a plurality of mapping electrodes configured to detect activation signals of intrinsic cardiac activity, each of the plurality of mapping electrodes having an electrode location;
    a mapping processor associated with the plurality of mapping electrodes, the mapping processor configured to record the detected activation signals and associate one of the plurality of mapping electrodes with each recorded activation signal, the mapping processor further configured to analyze the recorded activation signals to identify at least one recurring pattern of the detected activation signals sensed by mapping electrodes at different electrode locations based on a relationship between a timing of the detected activation signals and the electrode locations of the mapping electrode associated with each detected activation signal.

8. The catheter system according to claim 7, wherein the mapping processor is further configured to determine a location of the at least one frequently occurring pattern based on the location of the mapping electrodes and the corresponding detected activation signals.

9. The catheter system according to claim 7, wherein the mapping processor is further configured to correlate the at least one recurring pattern to at least one rotor template to determine whether the at least one recurring pattern is indicative of a dominant rotor.

10. The catheter system according to claim 9, wherein the mapping processor is configured to correlate the at least one recurring pattern to the at least one rotor template based on activation signals detected by a subset of the plurality of mapping electrodes.

11. The catheter system according to claim 9, wherein the rotor template is characteristic of at least one of a dominant rotor, rotor core, and rotor pathway having a cyclical and/or curvilinear pathway.

12. The catheter system according to claim 7, wherein the mapping processor is configured to run a sequential mining algorithm on the detected activation signals to identify at least one recurring pattern.

13. The catheter system according to claim 7, wherein the mapping processor is configured to run a location association mining algorithm on the detected activation signals to identify at least one recurring pattern.

14. The catheter system according to claim 7, wherein the mapping processor is configured to run a location association mining algorithm and a sequential mining algorithm on the detected activation signals to identify at least one recurring pattern.

15. A method for anatomical mapping comprising:
 positioning a plurality of mapping electrodes proximate to an anatomical structure, each of the plurality of mapping electrodes having an electrode location;
 detecting activation signals of intrinsic physiological activity within the anatomical structure;
 recording the detected activation signals and associating one of the plurality of mapping electrodes with each recorded activation signal; and
 analyzing the recorded activation signals to identify at least one recurring pattern of the detected activation signals sensed by mapping electrodes at different electrode locations based on a relationship between a timing of the detected activation signals and the electrode locations of the mapping electrode associated with each detected activation signal.

16. The method of claim 15, further including:
 determining a location of the at least one recurring pattern with respect to the anatomical structure.

17. The method of claim 15, further including:
 correlating the at least one recurring pattern to at least one pathology template to determine whether the at least one recurring pattern is indicative of a pathology.

18. The method of claim 17, wherein the at least one recurring pattern is correlated to the at least one pathology template based on activation signals detected by a subset of the plurality of mapping electrodes.

19. The method of claim 15, wherein a sequential mining algorithm is performed on the detected activation signals to identify the at least one recurring pattern.

20. The method of claim 15, wherein a location association mining algorithm is performed on the detected activation signals to identify at least one recurring pattern.

* * * * *